(12) United States Patent
Gray et al.

(10) Patent No.: US 8,377,994 B2
(45) Date of Patent: *Feb. 19, 2013

(54) USE OF ROLL COMPACTED PYROGENICALLY PRODUCED SILICON DIOXIDE IN PHARMACEUTICAL COMPOSITIONS

(75) Inventors: Ann Gray, Hanau (DE); Margarete Drechsler, Gelnhausen (DE); Ralph Hofmann, Buchen (DE)

(73) Assignee: Evonik Degussa GmeH, Essen (DE)

( * ) Notice: Subject to any disclaimer, the term of this patent is extended or adjusted under 35 U.S.C. 154(b) by 461 days.

This patent is subject to a terminal disclaimer.

(21) Appl. No.: 12/299,997

(22) PCT Filed: May 10, 2006

(86) PCT No.: PCT/EP2006/062215
§ 371 (c)(1),
(2), (4) Date: Jun. 25, 2009

(87) PCT Pub. No.: WO2007/128349
PCT Pub. Date: Nov. 15, 2007

(65) Prior Publication Data
US 2009/0306224 A1    Dec. 10, 2009

(51) Int. Cl.
*A61K 47/00* (2006.01)
*A61K 31/19* (2006.01)
*A61K 9/20* (2006.01)

(52) U.S. Cl. .................. 514/770; 514/571; 424/465
(58) Field of Classification Search .............. 514/770, 514/571; 424/465
See application file for complete search history.

(56) References Cited

U.S. PATENT DOCUMENTS

| | | |
|---|---|---|
| 3,738,785 A | 6/1973 | Reinhardt et al. |
| 3,742,566 A | 7/1973 | Reinhardt et al. |
| 3,762,851 A | 10/1973 | Reinhardt et al. |
| 3,860,682 A | 1/1975 | Reinhardt et al. |
| 4,325,686 A | 4/1982 | Leon et al. |
| 4,877,595 A | 10/1989 | Klingle et al. |
| 2004/0022844 A1* | 2/2004 | Hasenzahl et al. ............ 424/452 |
| 2005/0074386 A1 | 4/2005 | Valero |

FOREIGN PATENT DOCUMENTS

| | | |
|---|---|---|
| JP | 2005-508977 A | 4/2005 |
| JP | 2005-512935 A | 5/2005 |
| JP | 2009-536164 A | 10/2009 |
| WO | WO-99/44580 A | 9/1999 |
| WO | 03037379 A1 | 5/2003 |
| WO | WO-03/037379 A | 5/2003 |

(Continued)

OTHER PUBLICATIONS

Japanese Office Action received in JP2009-508145, mailed in Dec. 1, 2011.

(Continued)

*Primary Examiner* — Shirley V Gembeh
(74) *Attorney, Agent, or Firm* — Smith, Gambrell & Russell, LLP

(57) ABSTRACT

The use of Schülpen based on pyrogenically produced silicon dioxide in pharmaceutical compositions is described.

6 Claims, 6 Drawing Sheets

FOREIGN PATENT DOCUMENTS

| WO | 03055801 A1 | 7/2003 |
| WO | 2004039349 A1 | 5/2004 |
| WO | 2007128349 A1 | 11/2007 |

OTHER PUBLICATIONS

Jonat et al. "Investigation of the Glidant Properties of Compacted Colloidal Silicon . . . " European Journal of Pharmaceuticals . . . , vol. 63, No. 3, Mar. 3, 2006; pp. 356-359.

Jonat et al. "Inventigation of Compacted Hydrophilic and Hydrophobic colloidal . . . ", Powder Technology, Mar. 18, 2004; pp. 31-43.

Takashima Y. et al. "Reduction of Tablet Coloration at Tableting for Oily Medicine", International Journal of Pharmaceutics, Amsterdam, NL; vol. 187, No. 1; 1999; pp. 125-135.

Degussa "Product Information"—online 2006-2007, p. 1-10.

Jonat, Stephane "The Mecanism of Hydrophilic and Hydrophobic Colloidal"—online 2005, pp. 1-165.

* cited by examiner

Diagram of the construction of the sedimentation dust meter

USE OF ROLL COMPACTED PYROGENICALLY PRODUCED SILICON DIOXIDE IN PHARMACEUTICAL COMPOSITIONS

INTRODUCTION AND BACKGROUND

The present invention relates to the use of Schülpen of pyrogenic silicic acid in pharmaceutical compositions. The Schülpen are used in this connection in particular as glidants to improve the bulk flow of powders.

In a medicament it is generally possible to distinguish two functionally different substance groups, namely active ingredients and auxiliary substances.

Active ingredients are characterised by their specific pharmacological activity. They represent the active constituent of a medicament. As such, they are also identified quantitatively on the packaging and on the package leaflet.

Auxiliary substances, on the other hand, have no pharmacological activity. They are necessary in order to enable a suitable form of administration, namely the medicament, to be produced for the active ingredient. In general, the medicament contains a plurality of auxiliary substances having different functions. For example, auxiliary substances are used as fillers, binders, disintegrators, glidants, lubricants or release agents.

When developing stable, effective medicaments which are easy to handle from active ingredient(s) and auxiliary substances, there are a large number of auxiliary substances which can be used.

Highly disperse, pyrogenic silicon dioxide, for example Aerosil®, is frequently used in pharmaceutical and cosmetic compositions. In solid product forms it can be used as a flow regulator, adsorbent and drying agent; in liquid and semi-liquid product forms it can be used as a suspension stabiliser, framework-forming agent and gel-forming agent. It can also be used to increase the mechanical stability and the rate of disintegration of tablets. In addition, it can improve the distribution of the active ingredient.

A particular disadvantage when working with highly disperse silicon dioxide is the formation of dust, because very high demands have to be met in terms of cleanliness when producing pharmaceutical and cosmetic products.

A further disadvantage is the agglomeration behaviour of highly disperse silicon dioxide, which causes the product to come together as a result of hydrogen bridges and electrostatic charging. This results in larger lumps which do not pass through the relatively small sieve openings typical for the pharmaceutical industry. This is a particular problem in the case of silicon dioxides which have been compressed in order to minimise dust formation and have a higher bulk and tamped density.

Sieving is very important in order to eliminate foreign bodies in pharmaceutical products. As a result, modern automatic weighing and screening devices cannot be used, which increases the possibility of contamination from human handling.

When using highly dispersed silicon dioxide in pharmaceutical compositions improved flowability of mixtures prepared therewith would also be desirable in order to be able to achieve greater metering accuracy, for example when producing tablets and capsules. As a result it would be possible on the one hand to achieve lower variance of tablet and capsule weights and on the other hand to improve the economy of processes that result in such forms of administration.

SUMMARY OF THE INVENTION

The object of the present invention is to provide pharmaceutical compositions which avoid the disadvantages of the prior art.

The object is achieved by producing and using pharmaceutical compositions which contain Schülpen of pyrogenic silicon dioxide as auxiliary substance and which have a low dust content and at the same time can readily be sieved.

It has been found that, when working with the compositions according to the invention, almost no dust formation occurs, the Schülpen can readily be sieved and are not retained on the surface of the sieve, and the flowability of the compositions is equally as good as that of compositions according to the prior art. In addition, the mechanical stability of tablets is ensured, and even abrasion in the tablet-forming machine is reduced compared with the prior art.

The Schülpen of pyrogenic silicon dioxide as auxiliary substance are preferably present in the composition according to the invention in an amount of from 0.1 to 10 wt. %.

The composition according to the invention can additionally contain conventional auxiliary substances used in pharmacy, such as, for example, fillers such as carbohydrates, sugar alcohols, starches and starch derivatives; binders, such as, for example, gelatin, cellulose, polyvinylpyrrolidone derivatives; disintegrators, such as, for example, carboxymethylcellulose, maize starch and sodium carboxymethyl starch; glidants, such as, for example, talcum or polyethylene glycols; lubricants and release agents, such as, for example, magnesium or calcium stearate or stearic acid.

Processes for the production of pyrogenic silicon dioxide are to be found, for example, in Ullmann's Encyclopedia of Industrial Chemistry, Vol. A23, page 635 ff, 5th edition, 1993.

By subsequent treatment with a surface-modifying reagent it is also possible for the silicon dioxide to acquire a surface that has been rendered partially or completely hydrophobic. Processes relating thereto are to be found, for example, in DE-A 11 63 784, DE-A 196 16 781, DE-A 197 57 210 or DE-A 44 02 370.

It is possible to use for the compositions according to the invention also mixtures of pyrogenic silicon dioxide with doped silicon dioxide having an $SiO_2$ content of 90%, with mixed oxides having an $SiO_2$ content of 90% or more and/or silicon dioxide that has been rendered hydrophobic.

The subject of the invention is the use of Schülpen based on pyrogenically produced silicon dioxide in a pharmaceutical composition.

In an embodiment of the invention, the pyrogenically produced silicon dioxide compacted to form Schülpen can have a tamped density (according to DIN EN ISO 787-11) of from 185 to 700 g/l.

In a preferred embodiment of the invention, the tamped density (according to DIN EN ISO 787-11) can be from 200 to 450 g/l.

Schülpen refers to the more or less band-like intermediates that are formed during roller compaction by pressing of the starting material. They are comminuted in a second step.

The properties of the Schülpen can be influenced by the procedural parameter, such as the permitted mode of process control, the compaction force, the width of the gap between the two rollers and the pressure maintenance time, which is adjusted by appropriately changing the speeds of rotation of the press rollers.

Compaction is understood as meaning mechanical compression without the addition of binders. In a particular embodiment of the invention, the Schülpen have a defined shape, whereby the size distribution can be adjusted by means of sieving.

The pyrogenically produced silicon dioxide compacted to form Schülpen that is used according to the invention has high stability to transportation.

The pyrogenically produced silicon dioxide compacted to form Schülpen and having a tamped density (according to DIN EN ISO 787-11) of from 185 to 700 g/l can be produced by subjecting pyrogenically produced silicon dioxide to preliminary de-aeration, or pre-compression, compacting it to form Schülpen, breaking the Schülpen and optionally grading them.

BRIEF DESCRIPTION OF DRAWINGS

A diagrammatic representation of the process of the invention is shown in FIG. 1.

DETAILED DESCRIPTION OF INVENTION

Figure 1:
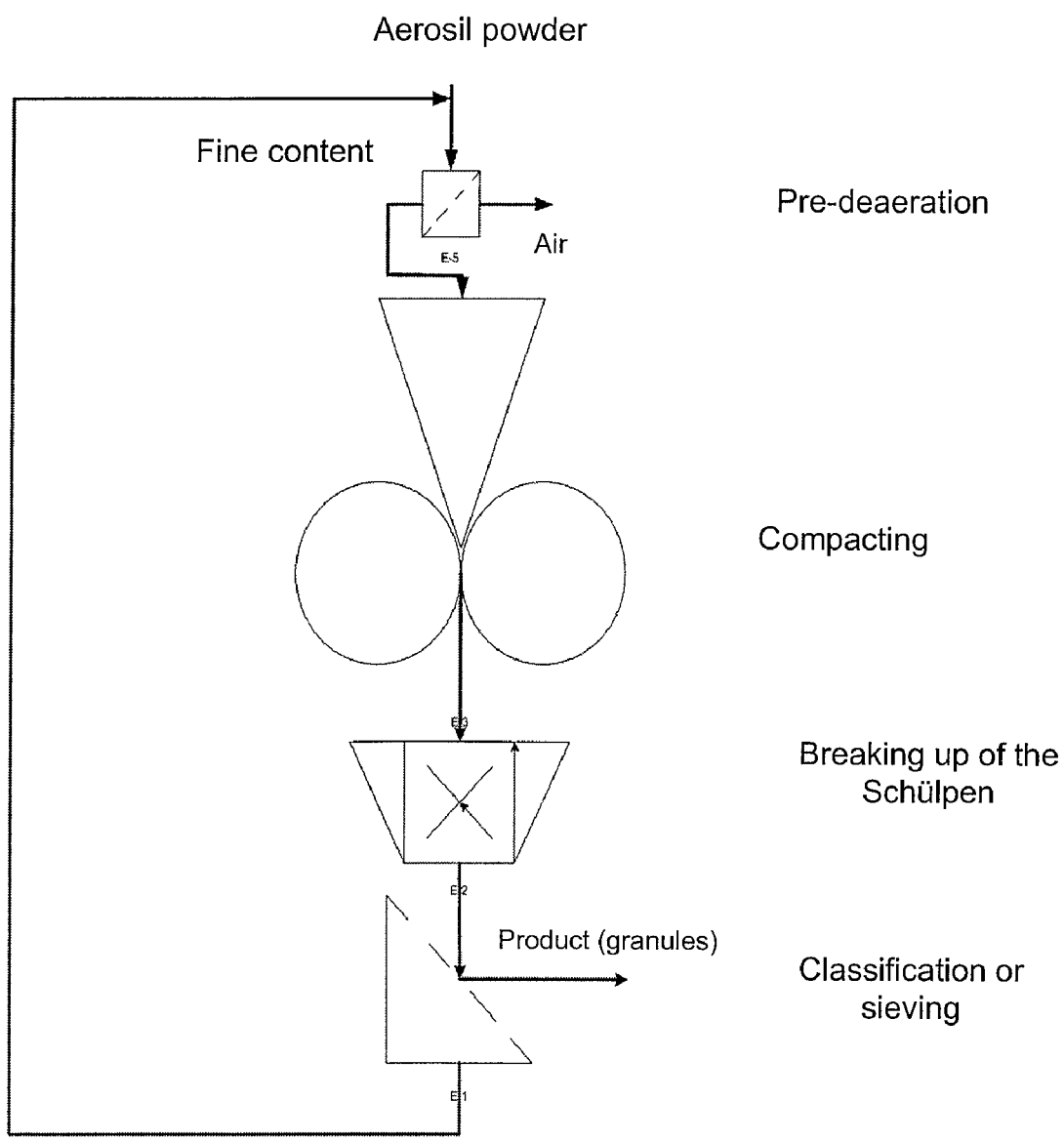

According to FIG. 1, the pyrogenically produced silicon dioxide is de-aerated, or pre-compressed, in the "preliminary de-aeration" step by means of known methods. This step is necessary when an uncompressed pyrogenically produced, optionally freshly produced, silicon dioxide is used.

If a pyrogenically produced silicon dioxide that has already been pre-compressed is used, the step of preliminary de-aeration can be omitted.

The pyrogenically produced silicon dioxide that has been subjected to preliminary de-aeration is compressed (compacted) to the desired tamped density in the "compaction" step.

After compaction, the Schülpen are broken. They can then be graded or sieved, if desired.

The fines content obtained during sieving can be fed back to the preliminary de-aeration step.

The starting material used in the preliminary de-aeration can be either an uncompressed or a pre-compressed silicon dioxide.

Preliminary de-aeration can be carried out either before transportation or during transportation to the compaction step.

Before transportation to the compaction step, preliminary de-aeration can be carried out by means of a pipe of a sintered material, such as, for example, sintered metal, to which a vacuum is applied.

Preliminary de-aeration can also take place in the screw conveyor, it being possible for the screw conveyor to be located downstream of the device comprising a pipe to which a vacuum is applied.

In a further embodiment, the screw conveyor can be used as the only device for preliminary de-aeration.

It is further possible for preliminary de-aeration to be carried out by means of a screw conveyor that is arranged inside a pipe to which a vacuum is applied. The pipe to which a vacuum is applied can consist of a sintered jacket, such as, for example, sintered metal.

When the device consists of a preliminary de-aeration pipe, for example a pipe to which a vacuum is applied, and a screw conveyor located downstream, the preliminary de-aeration can take place in the pipe if uncompressed silicon dioxide is used.

If pre-compressed silicon dioxide is used, preliminary de-aeration can likewise take place in the pipe. It is also possible to dispense with this preliminary de-aeration step.

If only the screw conveyor is used for the preliminary de-aeration, pre-compressed silicon dioxide must be used.

If preliminary de-aeration is carried out using the device comprising a screw conveyor inside a pipe to which a vacuum is applied, it is possible to use both uncompressed silicon dioxide and pre-compressed silicon dioxide.

Preliminary de-aeration of the pyrogenically produced silicon dioxide can further be carried out by means of filtration on a filter medium, such as, for example, a cloth or sintered material, such as, for example, sintered metal, sintered plastics material, sintered ceramics, porous glass, with continuous removal of the filter cake by, for example, a screw conveyor or a scraper. In an embodiment of the invention it is possible to use a sintered metal pipe with a metering screw.

Preliminary de-aeration can also be carried out by means of sedimentation, the breaking up of solids bridges being assisted by superimposed vibration, sound or slow stirring.

As starting material there can be used a hydrophilic pyrogenically produced silicon dioxide or a hydrophobic pyrogenically produced silicon dioxide.

Hydrophobic pyrogenically produced silicon dioxide can be produced by means of surface modification.

Surface modification can be effected using one or more compounds from the following group:

a) organosilanes of the type $(RO)_3Si(C_nH_{2n+1})$ and $(RO)_3Si(C_nH_{2n-1})$
R=alkyl, for example methyl, ethyl, n-propyl, isopropyl, butyl
n=1-20 b) organosilanes of the type $R'_x(RO)_ySi(C_nH_{2n+1})$ and $R'_x(RO)_ySi(C_nH_{2n-1})$
R=alkyl, for example methyl, ethyl, n-propyl, isopropyl, butyl
R'=alkyl, for example methyl, ethyl, n-propyl, isopropyl, butyl
R'=cycloalkyl
n=1-20
x+y=3
x=1,2
y=1,2 c) haloorganosilanes of the type $X_3Si(C_nH_{2n+1})$ and $X_3Si(C_nH_{2n-1})$
X=Cl, Br
n=1-20 d) haloorganosilanes of the type $X_2(R')Si(C_nH_{2n+1})$ and $X_2(R')Si(C_nH_{2n-1})$
X=Cl, Br
R'=alkyl, for example methyl, ethyl, n-propyl, isopropyl, butyl
R'=cycloalkyl
n=1-20 e) haloorganosilanes of the type $X(R')_2Si(C_nH_{2n+1})$ and $X(R')_2Si(C_nH_{2n-1})$
X=Cl, Br
R'=alkyl, for example methyl, ethyl,
R'=cycloalkyl n-propyl, isopropyl, butyl
n=1-20 f) organosilanes of the type $(RO)_3Si(CH_2)_m$—R'
  R=alkyl, such as methyl, ethyl, propyl
  m=0.1-20
  R'=methyl, aryl (for example —$C_6H_5$, substituted phenyl radicals)
    —$C_4F_9$, $OCF_2$—CHF—$CF_3$, —$C_6F_{13}$, —O—$CF_2$—$CHF_2$
    —$NH_2$, —$N_3$, —SCN, —CH=$CH_2$, —NH—$CH_2$—$CH_2$—$NH_2$,
    —N—($CH_2$—$CH_2$—$NH_2$)$_2$
    —OOC($CH_3$)C=$CH_2$
    —O$CH_2$—CH(O)$CH_2$
    —NH—CO—N—CO—($CH_2$)$_5$
    —NH—COO—$CH_3$, —NH—COO—$CH_2$—$CH_3$, —NH—($CH_2$)$_3$ Si(OR)$_3$
    —$S_X$—($CH_2$)$_3$Si(OR)$_3$, wherein X=from 1 to 10 and R=alkyl, such as methyl, ethyl, propyl, butyl
    —SH
    —NR'R"R''' (R'=alkyl, aryl; R"=H, alkyl, aryl; R'''=H, alkyl, aryl, benzyl, $C_2H_4$NR""R""' where R""=A, alkyl and R""'=H, alkyl)

g) organosilanes of the type $(R")_x(RO)_ySi(CH_2)_m$—R'
  R"=alkyl x+y=2
    =cycloalkyl x=1,2
    y=1,2
    m=from 0.1 to 20
  R'=methyl, aryl (for example —$C_6H_5$, substituted phenyl radicals)
    —$C_4F_9$, —$OCF_2$—CHF—$CF_3$, —$C_6F_{13}$, —O—$CF_2$—$CHF_2$
    —$NH_2$, —$N_3$, —SCN, —CH=$CH_2$, —NH—$CH_2$—$CH_2$—$NH_2$,
    —N—($CH_2$—$CH_2$—$NH_2$)$_2$—OOC($CH_3$)C=$CH_2$
    —O$CH_2$—CH(O)$CH_2$
    —NH—CO—N—CO—($CH_2$)$_5$
    —NH—COO—$CH_3$, —NH—COO—$CH_2$—$CH_3$, —NH—($CH_2$)$_3$ Si(OR)$_3$
    —$S_X$—($CH_2$)$_3$Si(OR)$_3$, wherein X=from 1 to 10 and R=methyl, ethyl, propyl, butyl
    —SH—NR'R" R''' (R'=alkyl, aryl; R'=H, alkyl, aryl; R'''=H, alkyl, aryl, benzyl, $C_2H_4$NR""R""' where R""=A, alkyl and R""'=H, alkyl)

h) haloorganosilanes of the type $X_3Si(CH_2)_m$—R'
  X=Cl, Br
  m=0.1-20
  R' methyl, aryl (for example —$C_6H_5$, substituted phenyl radicals)
    —$C_4F_9$, —$OCF_2$—CHF—$CF_3$, —$C_6F_{13}$, —O—$CF_2$—$CHF_2$
    —$NH_2$, —$N_3$, —SCN, —CH=$CH_2$,
    —NH—$CH_2$—$CH_2$—$NH_2$
    —N—($CH_2$—$CH_2$—$NH_2$)$_2$
    —OOC($CH_3$)C=$CH_2$
    —O$CH_2$—CH(O)$CH_2$
    —NH—CO—N—CO—($CH_2$)$_5$
    —NH—COO—$CH_3$, —NH—COO—$CH_2$—$CH_3$, —NH—($CH_2$)$_3$Si(OR)$_3$
    —$S_X$—($CH_2$)$_3$Si(OR)$_3$, wherein X=from 1 to 10 and R=methyl, ethyl, propyl, butyl
    —SH i) haloorganosilanes of the type $(R)X_2Si(CH_2)_m$—R'
  X=Cl, Br
  R=alkyl, such as methyl, ethyl, propyl
  m=0.1-20
  R'=methyl, aryl (e.g. —$C_6H_5$, substituted phenyl radicals)
    —$C_4F_9$, —$OCF_2$—CHF—$CF_3$, —$C_6F_{13}$, —O—$CF_2$—$CHF_2$
    —$NH_2$, —$N_3$, —SCN, —CH=$CH_2$, —NH—$CH_2$—$CH_2$—$NH_2$,
    —N—($CH_2$—$CH_2$—$NH_2$)$_2$
    —OOC($CH_3$)C=$CH_2$
    —O$CH_2$—CH(O)$CH_2$
    —NH—CO—N—CO—($CH_2$)$_5$
    —NH—COO—$CH_3$, —NH—COO—$CH_2$—$CH_3$,
    —NH—($CH_2$)$_3$Si(OR)$_3$, wherein R=methyl, ethyl, propyl, butyl
    —$S_X$—($CH_2$)$_3$Si(OR)$_3$, wherein R=methyl, ethyl, propyl, butyl and X=from 1 to 10
    —SH j) haloorganosilanes of the type $(R)_2X\,Si(CH_2)_m$—R'
  X=Cl, Br
  R=alkyl, such as methyl, ethyl, propyl, butyl
  m=0.1-20
  R'=methyl, aryl (e.g. —$C_6H_5$, substituted phenyl radicals)
    —$C_4F_9$, —$OCF_2$—CHF—$CF_3$, —$C_6F_{13}$, —O—$CF_2$—$CHF_2$
    —$NH_2$, —$N_3$, —SCN, —CH=$CH_2$, —NH—$CH_2$—$CH_2$—$NH_2$,
    —N—($CH_2$—$CH_2$—$NH_2$)$_2$
    —OOC($CH_3$)C=$CH_2$
    —O$CH_2$—CH(O)$CH_2$
    —NH—CO—N—CO—($CH_2$)$_5$
    —NH—COO—$CH_3$, —NH—COO—$CH_2$—$CH_3$,
    —NH—($CH_2$)$_3$ Si(OR)$_3$
    —$S_X$—($CH_2$)$_3$Si(OR)$_3$, wherein X=from 1 to 10 and R=methyl, ethyl, propyl, butyl
    —SH k) silazanes of the type R' $R_2$Si—N—Si$R_2$R'

R=alkyl
  R'=alkyl, vinyl l) cyclic polysiloxanes of the type D 3, D 4, D 5, wherein D 3, D 4 and D 5 are understood as being cyclic polysiloxanes having 3, 4 or 5 units of the type
  —O—Si($CH_3$)$_2$—.
  E.g. octamethylcyclotetrasiloxane=D 4

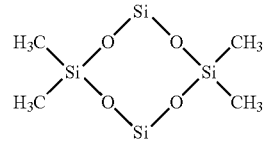

m) polysiloxanes or silicone oils of the type

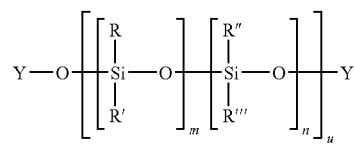

m=0, 1, 2, 3, . . . ∞
n=0, 1, 2, 3, . . . ∞
u=0, 1, 2, 3, . . . ∞
Y=$CH_3$, H, $C_nH_{2n+1}$ n=1-20

Y=Si(CH$_3$)$_3$, Si(CH$_3$)$_2$H
Si(CH$_3$)$_2$OH, Si(CH$_3$)$_2$(OCH$_3$)
Si(CH$_3$)$_2$(C$_n$H$_{2n+1}$)n=1-20
R=alkyl, such as C$_n$H$_{2n+1}$, wherein n=from 1 to 20, aryl, such as phenyl and substituted phenyl radicals, (CH$_2$)$_n$—NH$_2$, H
R'=alkyl, such as C$_n$H$_{2n+1}$, wherein n=from 1 to 20, aryl, such as phenyl and substituted phenyl radicals, (CH$_2$)$_n$—NH$_2$, H
R'=alkyl, such as C$_n$H$_{2n+1}$, wherein n=from 1 to 20, aryl, such as phenyl and substituted phenyl radicals, (CH$_2$)$_n$—NH$_2$, H
R'=alkyl, such as C$_n$H$_{2n+1}$, wherein n=from 1 to 20, aryl, such as phenyl and substituted phenyl radicals, (CH$_2$)$_n$—NH$_2$, H In an embodiment it is possible to use as starting material a pre-compressed pyrogenically produced silicon dioxide.

The uncompressed pyrogenically produced silicon dioxide that is used can have a tamped density (according to DIN EN ISO 787-11) of less than 50 g/l, preferably from 20 to 30 g/l. The pre-compressed pyrogenically produced silicon dioxide that is used can have a tamped density (according to DIN EN ISO 787-11) of from 50 to 190 g/l, preferably from 100 to 150 g/l, wherein the tamped density (according to DIN EN ISO 787-11) in the case of a pre-compressed hydrophobic pyrogenically produced silicon dioxide can be from 90 to 120 g/l.

The hydrophilic silicon dioxide that is used can have a tamped density (according to DIN EN ISO 787-11) of less than 50 g/l, preferably from 20 to 30 g/l, in the uncompressed state.

In the pre-compressed state, the hydrophilic silicon dioxide can have a tamped density (according to DIN EN ISO 787-11) of from 50 to 190 g/l, preferably from 100 to 150 g/l.

In the pre-compressed state, the hydrophobic silicon dioxide can have a tamped density (according to DIN EN ISO 787-11) of from 50 to 190 g/l, preferably from 90 to 120 g/l.

The pyrogenically produced silicon dioxide that is used can have a primary particle size of from 5 to 50 nm and a BET surface area of from 40 to 400 m$^2$/g, preferably from 100 to 250 m$^2$/g.

The water content of the pyrogenically produced silicon dioxide that is used can be less than 1 wt. %.

The pyrogenically produced silicon dioxide can be pre-compressed by means of known methods and devices. For example, the devices according to U.S. Pat. No. 4,325,686, U.S. Pat. No. 4,877,595, U.S. Pat. No. 3,838,785, U.S. Pat. No. 3,742,566, U.S. Pat. No. 3,762,851, U.S. Pat. No. 3,860,682 can be used.

In an embodiment, it is possible to use a pyrogenically produced silicon dioxide that has been pre-compressed by means of a press band filter according to EP 0280851 B1 or U.S. Pat. No. 4,877,595.

The pyrogenically produced silicon dioxide can be transported to the compaction step by means of a screw, for example.

This transport represents the forced guiding of the pyrogenically produced silicon dioxide into the roller gap of the compacting rollers. If a screw conveyor is not used, a pre-compressed pyrogenically produced silicon dioxide must be employed.

If a screw conveyor is used, the pyrogenically produced silicon dioxide does not have to be pre-compressed because preliminary de-aeration takes place therein.

In order to achieve high bulk weights of the Schülpen it is possible to use a screw conveyor and a pre-compressed pyrogenically produced silicon dioxide.

The screw conveyor used can be a screw with decreasing volume or with increasing pitch or with decreasing diameter.

The screw conveyor can be enclosed in a pipe to which a vacuum is applied. This pipe can consist of a sintered jacket. Preliminary de-aeration of the silicon dioxide here takes place in the screw conveyor at the same time as transportation into the roller gap.

Compaction to Schülpen can be carried out by means of two rollers, one or both of which can at the same time have a de-aerating function.

It is possible especially to use two compacting rollers, which can be smooth. They can also be profiled. The profile can be present either only on one compacting roller or on both compacting rollers.

The profile can consist of axis-parallel ribs. Alternatively, it can be troughs (indentations) of any desired form in any desired arrangement.

In a further embodiment, at least one of the rollers can be a vacuum roller. In this embodiment, the roller can be covered with sintered metal.

In order to carry out the de-aeration function, the roller can be produced from sintered metal or be covered with a filter medium, such as, for example, with a cloth.

If the pyrogenically produced silicon dioxide can be de-aerated by means of the rollers, it is possible to dispense with the additional preliminary de-aeration, which can take place in the screw conveyor or the feed pipe.

If the roller is used for preliminary de-aeration, the roller can have a smooth or profiled surface, it being possible for the surface to be only slightly ribbed in order to improve product intake.

During compaction, uniform compression of the pyrogenically produced silicon dioxide is to be ensured in order to obtain Schülpen of uniform density.

Figure 2:
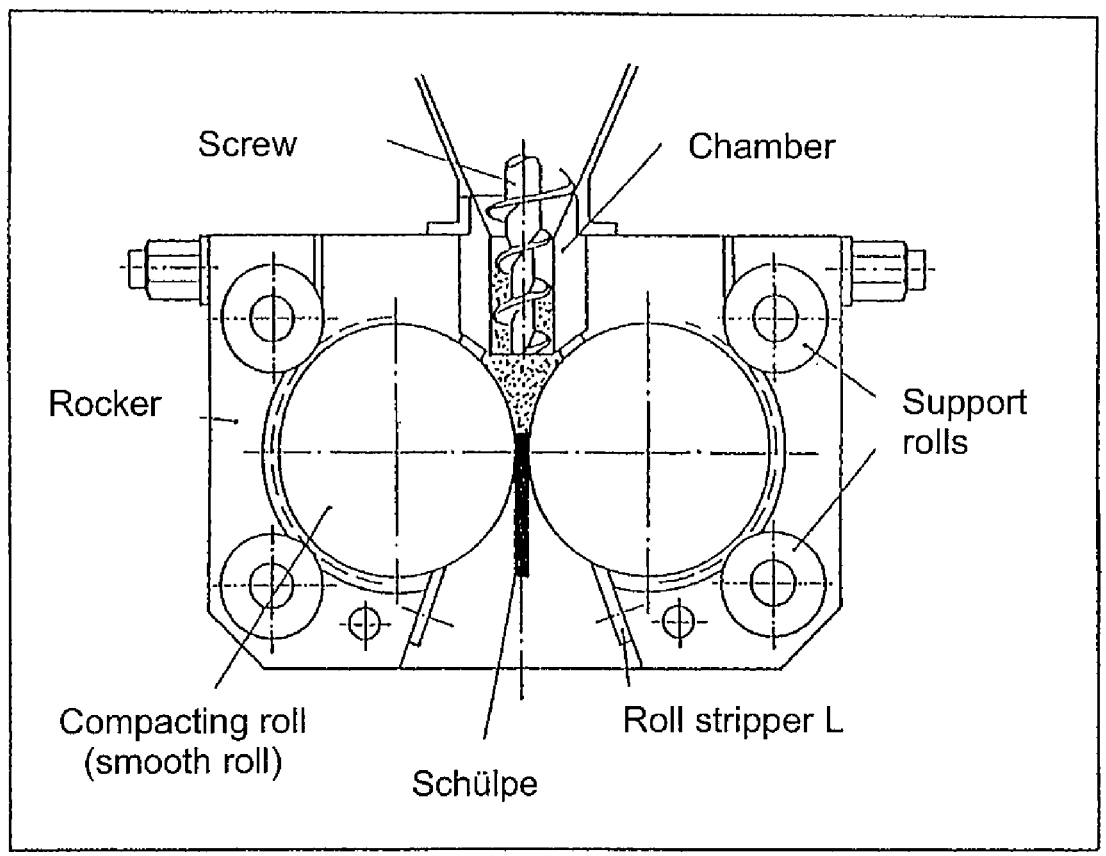
FIG. 2 illustrates the device which can be used to carry out the conjunction.

A device as shown in FIG. 2 can be used for carrying out the compaction.

According to FIG. 2, the pyrogenically produced silicon dioxide is introduced by means of the pre-compressor screw 1 into the chamber 2 between the two rollers 3 and is compressed between the two rollers to form Schülpen.

A device as described in document DE AS 1807714 can also be used for carrying out the process.

During compaction, smooth rollers can preferably be used in order to avoid grit. It is further possible to use one or two rollers of sintered material, such as sintered metal or sintered ceramics, via which de-aeration can take place.

After compaction, the Schülpen are broken. To this end there can be used a sieve granulator, which specifies the grain size by the mesh size of the sieve. The mesh size can be from 250 μm to 20 mm.

For breaking the Schülpen it is further possible to use a device having two rollers which rotate in opposite directions and have a defined gap between them, or a toothed roller.

The broken Schülpen can be graded by means of a sifter, a sieve or a classifier. The fines content (particles smaller than 200 μm) can be separated off thereby.

As sifters there can be used cross-flow sifters, countercurrent deflecting sifters, etc.

A cyclone can be used as classifier.

The fines content (particles smaller than 200 μm) separated off during grading can be fed back into the process according to the invention.

Determination of the Dust Content

The dust content is determined according to DIN 55992-2.

Prior to the measurement, a weighed amount of the Schülpen of the pyrogenically produced silicon dioxide to be tested is introduced into a feed system at the top end of the down pipe. This is closed at the bottom before the start of the measurement by flaps. The end of the down pipe is closed. At the start of the measurement, that flap is opened for a specific period of time so that the sample is able to fall into the down pipe. As it falls, and when it comes into contact with the bottom of the down pipe, the sample gives off dust into the air. The air currents during falling ensure that the dust is distributed uniformly in the pipe. The suspended material then begins to settle. At the bottom end of the down pipe, the light extinction caused by the suspended material is measured by a photometric sensor. The course of the sedimentation is indicated by a PC as a function of the time. In the case of the CIPACMT171 dust-measuring device, the extinction E (in %) is plotted directly as a function of the sedimentation time. In the case of the SP3 dust-measuring device from Lorenz, the dust number SZ is calculated according to the following formula (eq. 1) and plotted as a function of time.

$$SZ = 1 - \frac{\int_{1s}^{30s} E(t)dt - \int_{16s}^{30s} E(t)dt}{\int_{1s}^{30s} E(t)dt}$$

The dust number is a measure of the fine dust content of the sample. "Fine dust" here refers to the fraction whose rate of sedimentation in air is less than 1 m/16 s=0.0625 m/s.

Figure 3:
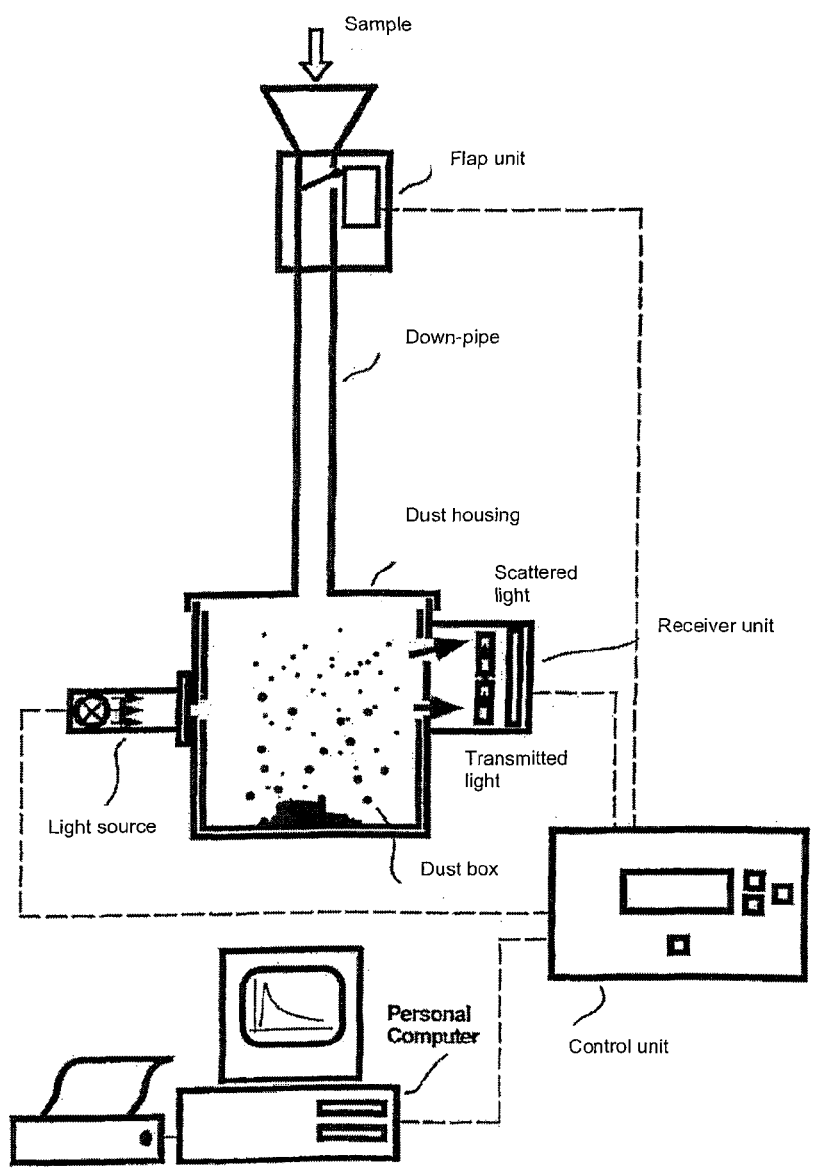
FIG. 3 is a diagrammatic representation of the device used to determine the dust content.

A diagrammatic representation of the device used to determine the dust content is shown in FIG. 3.

Figure 4:
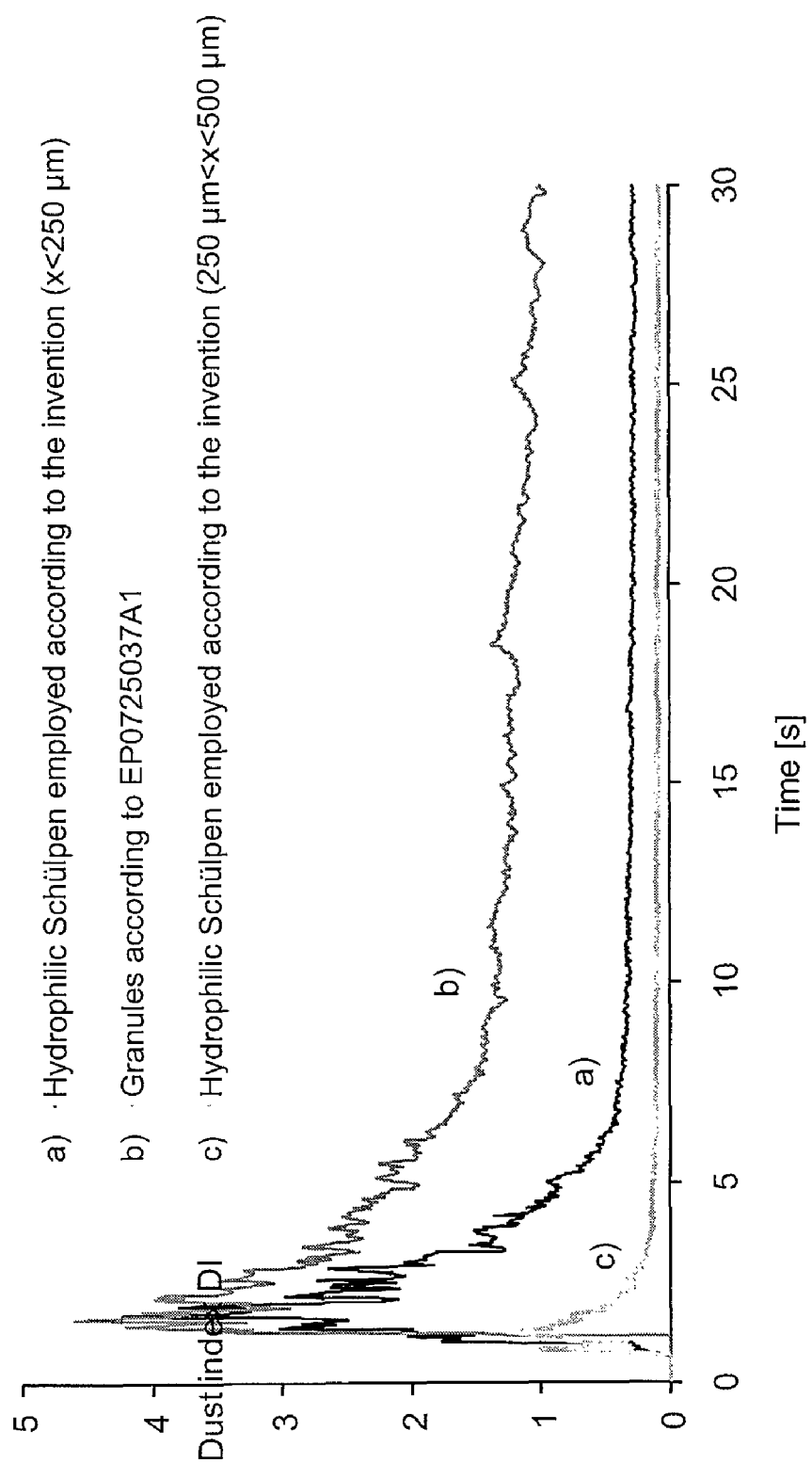
FIG. 4 shows a measure of the particle size distribution and the mean particle size of the bulk powder or Shülpen, which are used according to the invention.

In FIG. 4, the fine dust content of the pyrogenically produced silicon dioxide compacted to form Schülpen that is used according to the invention and the fine dust contents of pyrogenic silicon dioxide that has been compressed by a different method are compared.

The starting material employed for the silicon dioxide used according to the invention was a pyrogenically produced silicon dioxide that had been compressed by means of the press band filter according to EP 0280851 B1.

FIG. 4 shows a measure of the particle size distribution and the mean particle size of the bulk powder or Schülpen, which are used with the according to the invention. This demonstrates that the Schülpen of the pyrogenically produced silicon dioxide that are used according to the invention settle significantly better and form significantly less dust than the granules according to EP 0 725037 A1.

FIG. 4 also shows a measure of the fine or suspended dust content. This demonstrates that the suspended dust content can be drastically reduced with the Schülpen used according to the invention. In the case of granules according to EP 075 037 A1, a large proportion remains suspended for a long time.

Figure 5:
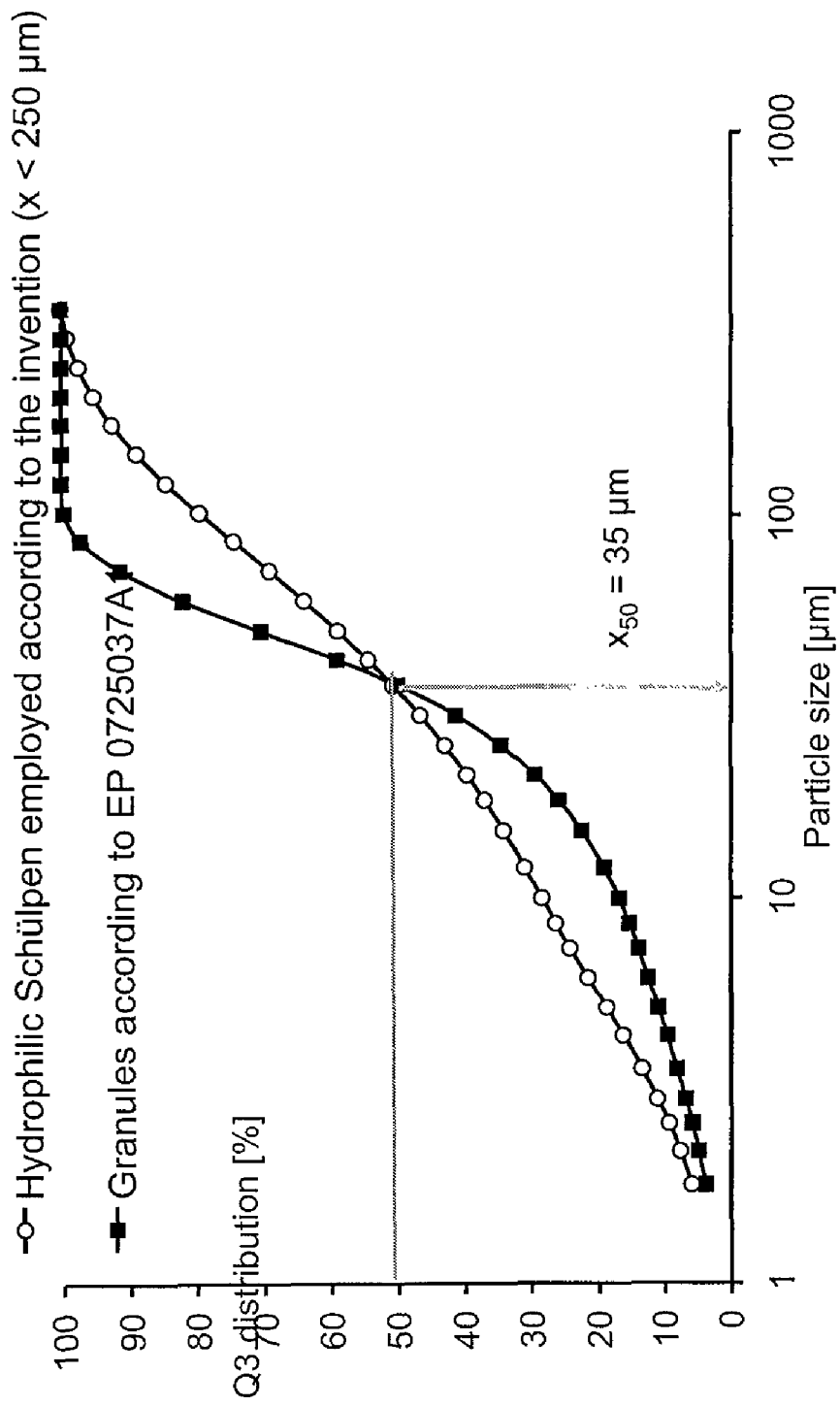
FIG. 5 shows the combined distribution (Q-3 distribution) of various granules according to EP 0 725 037 A1.

FIG. 5 shows the combined distribution (Q-3 distribution) of various granules according to EP 0 725 037 A1. None of these granules exhibits a mean particle size of 120 μm. Only the largest particles in this group are from 96 to 128 μm in size. This is less than 11%.

The Schülpen used according to the invention with X<250 μm have the same mean particle size as the granules according to EP 0 725 037 A1 in laser diffraction spectroscopy. In both cases it is ~35 μm.

However, the Schülpen according to the invention produce significantly less dust.

The fractions of the Schülpen were produced by sieve granulation using a sieve having a mesh size of 500 μm, with subsequent sieving on a 250 μm sieve. The fraction x<250 μm was the fine material during sieving. The fraction having a particle size of from 250 to 500 μm was the coarse material.

Figure 6:
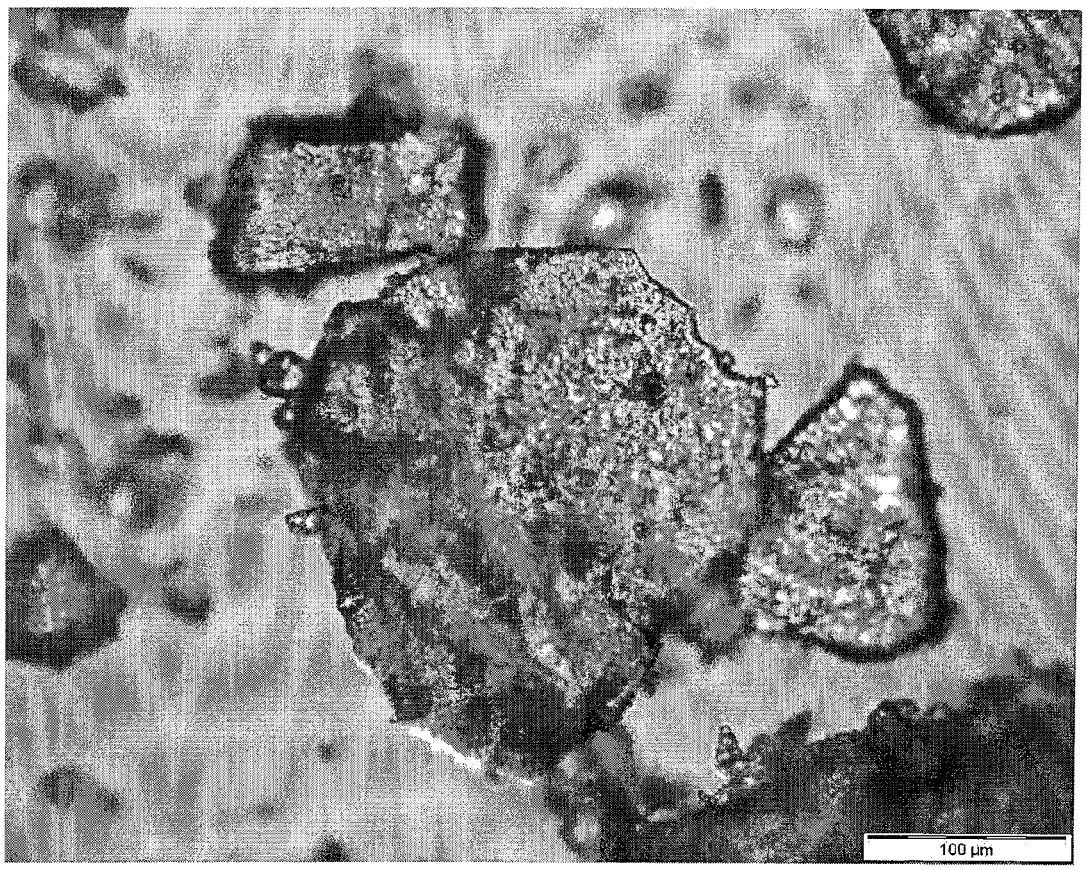
FIG. 6 shows the pyrogenically produced silicon dioxide compacted to form Shülpen that is used according to the invention, in its granular form after breaking and sieving.

FIG. 6 shows the pyrogenically produced silicon dioxide compacted to form Schülpen that is used according to the invention, in its granular form after breaking and sieving. It has an angular shape.

The granules according to DE 19601415 have a spherical appearance.

In a preferred embodiment, the Schülpen used according to the invention have a tamped density of from 200 to 300 g/l. Such Schülpen then have the necessary strength not to disintegrate again in the subsequent steps. However, they can readily be dispersed again.

Furthermore, the Schülpen that are obtained are porous.

The Schülpen used according to the invention have an advantageously low dust content after breaking even without sieving or grading.

The Schülpen used according to the invention have an agglomerate hardness of less than 50 N, measured using an ERWEKA 30.

After breaking, the Schülpen used according to the invention do not exhibit a further dust content. Even during handling, transportation or storage, no further dust content is formed with the Schülpen used according to the invention. The pyrogenically produced silicon dioxide compacted to form Schülpen does not exhibit a fines content having a diameter of less than 200 μm after sieving.

The pyrogenically produced silicon dioxide compacted to form Schülpen that is used according to the invention has a low dust content that is advantageous for all applications. It can be added to the mixtures without loss and without introducing dust.

The pyrogenically produced silicon dioxide compacted to form Schülpen does not contain binder.

The silicon dioxide utilized in the invention is of the very fine particle size variety. In the most preferred embodiments of the invention, the silicon dioxide utilized is a colloidal silicon dioxide. Colloidal silicon dioxide is a submicron fumed silica prepared by the vapor-phase hydrolysis (e.g., at 1110° C.) of a silicon compound, such as silicon tetrachloride. The product itself is a submicron, fluffy, light, loose, bluish-white, odorless and tasteless amorphous powder which is commercially available from a number of sources, including Cabot Corporation (under the tradename Cab-OSil); Degussa, Inc. (under the tradename AEROSIL); E.1. DuPont & Co.; and W.R. Grace & Co. Colloidal silicon dioxide is also known as colloidal silica, fumed silica, light anhydrous silicic acid, silicic anhydride, and silicon dioxide fumed, among others. A variety of commercial grades of colloidal silicon dioxide are produced by varying the manufacturing process. These modifications do not affect the silica content, specific gravity, refractive index, color or amorphous form. However, these modifications are known to change the particle size, surface areas, and bulk densities of the colloidal silicon dioxide products.

The surface area of the preferred dass of silicon dioxides utilized in the invention ranges from about 50 m$^2$/gm to about 500 m$^2$/gm. The average primary particle diameter of the preferred dass of silicon dioxides utilized in the invention ranges from about 5 nm to about 50 nm. However, in commercial colloidal silicon dioxide products, these particles are agglomerated or aggregated to varying extents. The bulk density of the preferred dass of silicon dioxides utilized in the invention ranges from about 20 g/l to about 100 g/l.

Commercially available colloidal silicon dioxide products have, for example, a BET surface area ranging from about 50±15 m$^2$/gm (AEROSIL OX50) to about 400±20 (Cab-O-Sil S-17) or 390±40 m$^2$/gm (Cab-O-Sil EH-5). Commercially available particle sizes range from a nominal particle diameter of 7 nm (e.g., Cab-O-Sil S-17 or Cab-O-Sil EH-5) to an average primary particle size of 40 nm (AEROSIL OX50). The density of these products range from 72.0±8 g/l (Cab-O-Sil S-17) to 36.8 g/l (e.g., Cab-O-Sil M-5). The pH of the these products at 4% aqueous dispersion ranges from pH 3.5-4.5.

The pyrogenic silicon dioxide serving as starting material is produced by feeding a volatile silicon compound through a nozzle into a detonating gas flame of hydrogen and air. Silicon tetrachloride is used in most cases. This substance hydrolyses under the influence of the water produced in the detonating gas reaction, to form silicon dioxide and hydrochloric acid. After leaving the flame the silicon dioxide enters a so-called coagulation zone in which the silicon dioxide primary particles and primary aggregates agglomerate. The product present as a form of aerosol in this stage is separated from the gaseous accompanying substances in cyclones and is then post-treated with moist hot air. The residual hydrochloric acid content can be reduced to below 0.025% by this process.

The granular materials (Schülpen) based on pyrogenically produced silicon dioxide may also be silanised. The carbon content of the granular material is then preferably 0.3 to 15.0 wt. %. Halogenated silantes, alkoxysilanes, silazanes and/or siloxanes may be used for the silanisation.

The following substances in particular may be used as halogenated silanes:
X=Cl, Br
n=1-20 halogenated organosilanes of the type $X_2(R')Si(C_nH_{2n+1})$
X=Cl, Br
R'=Alkyl
n=1-20 halogenated organosilanes of the type $X(R')_2Si(C_nH_{2n+1})$
X=C, Br
R'=Alkyl
n=1-20 halogenated organosilanes of the type $X_3Si(CH_2)_m$—R'
X=Cl, Br
m=0.1-20
R'=Alkyl, aryl (e.g. —$C_6H_5$)
—$C_4F_9$, —$OCF_2$—CHF—$CF_3$, —$C_6F_{13}$, —O—$CF_2$—$CHF_2$
—$NH_2$, —$N_3$, —SCN, —CH=$CH_2$,
—OOC($CH_3$)C=$CH_2$
—$OCH_2$—CH(O)$CH_2$

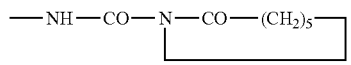

—NH—COO—$CH_3$,   —NH—COO—$CH_2$—$CH_3$,
—NH—($CH_2$)$_3$Si(OR)$_3$
—$S_X$—($CH_2$)$_3$ Si(OR)$_3$ halogenated organosilanes of the type $(R)X_2Si(CH_2)_m$—R'
X=Cl, Br
R=Alkyl
m=0.1-20
R'=Alkyl, aryl (e.g. —$C_6H_5$)
—$C_4F_9$, —$OCF_2$—CHF—$CF_3$, —$C_6F_{13}$, —O—$CF_2$—$CHF_2$
—$NH_2$, —$N_3$, —SCN, —CH=$CH_2$,
—OOC($CH_3$)C=$CH_2$
—$OCH_2$—CH(O)$CH_2$

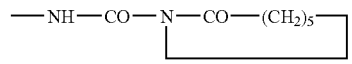

—NH—COO—$CH_3$,   —NH—COO—$CH_2$—$CH_3$,
—NH—($CH_2$)$_3$ Si(OR)$_3$
—$S_X$—($CH_2$)$_3$Si(OR)$_3$ halogenated organosilanes of the type $(R)_2X Si(CH_2)_m$—R'
X=Cl, Br
R=Alkyl
m=0.1-20
R'=Alkyl, aryl (e.g. —$C_6H_5$)
—$C_4F_9$, —$OCF_2$—CHF—$CF_3$, —$C_6F_{13}$, —O—$CF_2$—$CHF_2$
—$NH_2$, —$N_3$, —SCN, —CH=$CH_2$,
—OOC($CH_3$)C=$CH_2$
—$OCH_2$—CH(O)$CH_2$

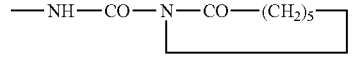

—NH—COO—$CH_3$,   —NH—COO—$CH_2$—$CH_3$,
—NH—($CH_2$)$_3$ Si(OR)$_3$
—$S_X$—($CH_2$)$_3$ Si(OR)$_3$

The following substances in particular may be used as alkoxysilanes:

organosilanes of the type $(RO)_3Si(C_nH_{2n+1})$
R=Alkyl
n=1-20 organosilanes of the type $R'_x(RO)_y Si(C_nH_{2n+1})$
R=Alkyl
R'=Alkyl
n=1-20
x+y=3
x=1.2
y=1.2 organosilanes of the type $(RO)_3 Si(CH_2)_m$—R'
R=Alkyl
m=0.1-20
R'=Alkyl, aryl (e.g. —$C_6H_5$)
—$C_4F_9$, $OCF_2$—CHF—$CF_3$,  —$C_6F_{13}$, —O—$CF_2$—$CHF_2$
—$NH_2$, —$N_3$, —SCN, —CH=$CH_2$,
—OOC($CH_3$)C=$CH_2$
—$OCH_2$—CH(O)$CH_2$

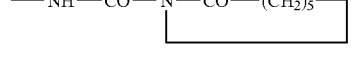

—NH—COO—$CH_3$,   —NH—COO—$CH_2$—$CH_3$,
—NH—($CH_2$)$_3$ Si(OR)$_3$
—$S_X$—($CH_2$)$_3$Si(OR)$_3$ organosilanes of the type $(R'')_x(RO)_y Si(CH_2)_m$—R'
R''=Alkyl
x+y=2
x=1.2
y=1.2
R'=Alkyl, aryl (e.g. —$C_6H_5$)
—$C_4F_9$, —$OCF_2$—CHF—$CF_3$, —$C_6F_{13}$, —O—$CF_2$—$CHF_2$
—$NH_2$, —$N_3$, —SCN, —CH=$CH_2$,
—OOC($CH_3$)C=$CH_2$
—$OCH_2$—CH(O)$CH_2$ —NH—CO—N—CO—(CH$_2$)$_5$—
  (with bracket connecting N to (CH$_2$)$_5$)

—NH—COO—CH$_3$,    —NH—COO—CH$_2$—CH$_3$,
—NH—(CH$_2$)$_3$ Si(OR)$_3$
—S$_x$—(CH$_2$)$_3$ Si(OR)$_3$

The silane Si 108 [(CH$_3$O)$_3$—Si—C$_8$H$_{17}$] trimethoxyoctylsilane may preferably be used as silanisation agent.

The following substances in particular may be used as silazanes:

Silazanes of the type:

R'R$_2$Si—N—SiR$_2$R''
         |
         H

R=Alkyl
R'=Alkyl, vinyl as well as for example hexamethyldisilazane.

The following substances in particular may be used as siloxanes:
cyclic polysiloxanes of the type D 3, D 4, D 5, e.g. octamethylcyclotetrasiloxane=D 4

(structure of octamethylcyclotetrasiloxane shown)

polysiloxanes and/or silicone oils of the type:

$$Y-O-\left[\left[\begin{array}{c}R\\|\\Si-O\\|\\R'\end{array}\right]_m \left[\begin{array}{c}R''\\|\\Si-O\\|\\R'''\end{array}\right]_n\right]_u -Y$$

R=Alkyl, aryl, (CH$_2$)$_n$—NH$_2$, H
R'=Alkyl, aryl, (CH$_2$)$_n$—NH$_2$, H
R'=Alkyl, aryl, (CH$_2$)$_n$—NH$_2$, H
R'=Alkyl, aryl, (CH$_2$)$_n$—NH$_2$, H
Y=CH$_3$, H, C$_n$H$_{2n+1}$ where n=1-20
Y=Si(CH$_3$)$_3$, Si(CH$_3$)$_2$H
  Si(CH$_3$)$_2$OH, Si(CH$_3$)$_2$(OCH$_3$)
  Si(CH$_3$)$_2$(C$_n$H$_{2n+1}$) where n=1-20
m=0, 1, 2, 3, ... ∞
n=0, 1, 2, 3, ... ∞
u=0, 1, 2, 3, ... ∞

The silanisation may be carried out by spraying the Schülpen with the silanisation agent, which may optionally be dissolved in an organic solvent, for example ethanol, and then thermally treating the mixture at a temperature of 105° to 400° C. for a period of 1 to 6 hours.

An alternative method of silanising the Schülpen involves treating the Schülpen with the silanisation agent in vapour form and then thermally treating the mixture at a temperature of 200° to 800° C. for a period of 0.5 to 6 hours. The thermal treatment may be carried out under a protective gas, such as for example nitrogen.

The silanisation may be carried out continuously er batchwise in heatable mixers and dryers with spray devices. Suitable types of apparatus include for example ploughshare mixers, plate dryers, fluidised-bed dryers or turbulent-layer dryers.

The physicochemical parameters of the Schülpen, such as the specific surface, grain size distribution, pore volume, tamped density and silanol group concentration, pore distribution and pH value may be altered within the specified limits by varying the starting substances, spraying conditions, heat treatment and silanisation.

One subject of the invention is the use of Schülpen based on pyrogenically produced silicon dioxide in a pharmaceutical composition.

Thereby the pharmaceutical composition can be present in the form of a suspension, emulsion, aerosol, ointment, cream, gel, paste, suppository, stick, powder, topical powder, granular material, tablet, pastille, sugar-coated pill, film-coated tablet, hard gelatin capsule, soft gelatin capsule, extrudate, microcapsule or a microsphere.

According to the invention the Schülpen can act as a glidant for pharmaceutical active constituents and/or auxiliary substances.

A further subject of the invention is a pharmaceutical composition containing Schülpen based on pyrogenically produced silicon dioxide and at least one pharmaceutical active constituent.

The pharmaceutical composition according to the invention can contain furthermore at least one pharmaceutical auxiliary substance.

The silicon dioxide Schülpen may be used in combination with any arbitrary pharmaceutical active constituent. The following may be mentioned by way of example:

a-proteinase inhibitor, abacavir, abciximab, acarbose, acetylsalicylic acid, acyclovir, adenosine, albuterol, aldesleukin, alendronate, alfuzosin, alosetrone, alprazolam, alteplase, ambroxol, amifostine, amiodarone, amisulprid, amlodipine, amoxicillin, amphetamine, amphotericin, ampicillin, amprenavir, anagrelide, anastrozole, ancrod, anti-haemophilia factor, aprotinin, atenolol, atorvastatin, atropine, azelastine, azithromycin, azulene, barnidipin, beclomethasone, benazepril, benserazide, beraprost, betamethasone, betaxolol, bezafibrate, bicalutamide, bisabolol, bisoprolol, botulinum toxin, brimonidine, bromazepam, bromocriptine, budesonide, bupivacaine, bupropion, buspirone, butorphanol, cabergoline, calcipotriene, calcitonin, calcitriol, camphor, candesartan, candesartan cilexetil, captopril, carbamazepine, carbidopa, carboplatin, carvedilol, cefaclor, cefadroxil, cefaxitin, cefazolin, cefdinir, cefepime, cefixime, cefmetazole, cefoperazone, cefotiam, cefoxopran, cefpodoxime, cefprozil, ceftazidime, ceftibuten, ceftriaxone, cefuroxime, celecoxib, celiprolol, cephalexin, cerivastatin, cetirizine, chloramphenicol, cilastatin, cilazapril, cimetidine, ciprofibrate, ciprofloxacin, cisapride, cisplatin, citalopram, clarithromycin, clavulanic acid, clindamycin, clomipramine, clonazepam, clonidine, clopidogrel, clotrimazole, clozapine, cromolyn, cyclophosphamide, cyclosporine, cyproterone, dalteparin, deferoxamine, desogestrel, dextroamphetamine, diazepam, diclofenac, didanosine, digitoxin, digoxin, dihydroergotamine, diltiazem, diphtheria protein, diphtheria toxoide, divalproex, dobutamine, docetaxel, dolasetron, donepezil, dornase-a, dorzolamide, doxazosin, doxifluridin, doxorubicin, dydrogesterone, ecabet, efavirenz, enalapril, enoxaparin, eperisone, epinastin, epirubicin, eptifibatide, erythropoietin-a, erythropoietin-β, etanercept, ethinyl oestradiol, etodolac, etoposide, factor VIII, famciclovir, famotidine, faropeneme, felodipine, fenofibrate, fenoldopam, fentanyl, fexofenadin, filgrastim, finasteride, flomoxef, fluconazole, fludarabine, flunisolide, flunitrazepam, fluoxetine, flutamide, fluticasone, fluvastatin, fluvoxamine, follitropin-a, follitropin-β, formoterol, fosinopril, furosemide, gabapentin, gadodiamide, ganciclovir, gatifloxacin, gemcitabine, gestoden, glatiramer, glibenclamide, glimepiride, glipizide, glyburide, goserelin, granisetron, griseofulvin, hepatitis B antigen, hyaluronic acid, hycosin, hydrochlorothiazide, hydrocodone, hydrocortisone, hydromorphone, hydroxychloroquine, hylan G-F 20, ibuprofen, ifosfamide, imidapril, imiglucerase, imipenem, immunoglobulin, indinavir, indomethacin, infliximab, insulin, insulin human, insulin Lispro, insulin aspart, interferon β, interferon a, iodine 125, iodixanol, iohexyl, iomeprol, iopromid, ioversol, ioxoprolen, ipratropium, ipriflavone, irbesartan, irinotecan, isosorbide, isotretinoin, isradipine, itraconazole, potassium clorazepate, potassium chloride, ketorolac, ketotifen, whooping cough vaccine, coagulation factor IX, lamivudine, lamotrigine, lansoprazole, latanoprost, leflunomide, lenograstim, letrozole, leuprolide, levodopa, levofloxacin, levonorgestrel, levothyroxine, lidocaine, linezolid, lisinopril, lopa-midol, loracarbef, loratadine, lorazepam, losartan, lovastatin, lysineacetylsalicylic acid, manidipin, mecobalamin, medroxyprogesterone, megestrol, meloxicam, menatetrenone, meningococcus vaccine, menotropine, meropenem, mesalamine, metaxalone, metformin, methylphenidate, methylprednisolone, metoprolol, midazolam, milrinone, minocycline, mirtazapine, misoprostol, mitoxantrone, moclobemid, modafinil, mometasone, montelukast, morniflumat, morphine, moxifloxacin, mycophenolate, nabumetone, nadroparin, naproxen, naratriptan, nefazodone, nelfinavir, nevirapine, niacin, nicardipine, nicergoline, nifedipine, nilutamide, nilvadipine, nimodipine, nitroglycerin, nizatidine, norethindrone, norfloxacin, octreotide, olanzapine, omeprazole, ondansetron, orlistate, oseltamivir, oestradiol, oestrogens, oxaliplatin, oxaprozin, oxolinic acid, oxybutynin, paclitaxel, palivizumab, pamidronate, pancrelipase, panipenem, pantoprazol, paracetamol, paroxetine, pentoxifylline, pergolide, phenyloin, pioglitazon, piperacillin, piroxicam, pramipexole, pravastatin, prazosin, probucol, progesterone, propafenone, propofol, propoxyphene, prostaglandin, quetiapine, quinapril, rabeprazol, raloxifene, ramipril, ranitidine, repaglinide, reserpine, ribavirin, riluzole, risperidone, ritonavir, rituximab, rivastigmin, rizatriptan, rofecoxib, ropinirol, rosiglitazone, salmeterol, saquinavir, sargramostim, serrapeptase, sertraline, sevelamer, sibutramin, sildenafil, simvastatin, somatropine, sotalol, spironolactone, stavudin, sulbactam, sulfaethidole, sulfamethoxazole, sulfasalazin, sulpirid, sumatriptan, tacrolimus, tamoxifen, tamsulosin, tazobactam, teicoplanin, temocapril, temozolomid, tenecteplase, tenoxicam, teprenon, terazosin, terbinafine, terbutaline, tetanus toxoid, tetrabenazine, tetrazepam, thymol, tiagabine, tibolon, ticarcillin, ticlopidine, timolol, tirofiban, tizanidine, tobramycin, tocopheryl nicotinate, tolterodine, topiramate, topotecan, torasemid, tramadol, trandolapril, trastuzumab, triamcinolone, triazolam, trimebutin, trimethoprim, troglitazone, tropisetrone, tulobuterol, unoproston, urofollitropine, valacyclovir, valproic acid, valsartan, vancomycin, venlafaxine, verapamil, verteporfin, vigabatrin, vinorelbine, vinpocetine, vitamin A, vitamin D, vitamin E, vitamin K, voglibose, warfarin, zafirlukast, zaleplon, zanamivir, zidovudine, zolmitriptan, zolpidem, zopiclone nutritional oils, essential fatty acids, non-essential fatty acids, extracts of plant or animal origin, oils of plant or animal origin and their derivatives.

Pharmaceutical active constituents are however also understood to include other substances such as vitamins, provitamins, essential fatty acids, extracts of plant and animal origin and oils of plant and animal origin.

Suitable active pharmaceutical ingredients are not limited by therapeutic category, and can be, for example, analgesics, anti-inflammatory agents, antihelminthics, anti-arrhythmic agents, anti-bacterial agents, anti-viral agents, anticoagulants, anti-depressants, anti-diabetics, anti-epileptics, antifungal agent, anti-gout agents, anti-hypertensive agents, antimalarials, anti-migraine agents, anti-muscarinic agents, antineoplastic agents, erectile dysfunction improvement agents, immunosuppresants, anti-protozoal agents, antithyroid agents, anxiolytic agents, sedatives, hypnotics, neuroleptics, β-blockers, cardiac inotropic agents, corticosteroids, diuretics, anti-parkinsonian agents, gastrointestinal agents, histamine receptor antagonists, keratolytics, lipid regulating agents, anti-anginal agents, Cox-2 inhibitors, leukotriene inhibitors, macrolides, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, extracts of plant or animal origin, oils of plant or animal origin, and mixtures thereof.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), antiemetics (e.g., metoclopramide), antiepileptics (e.g., phenyloin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluazide), antihypotensives (e.g., propranolol, clonidine), antihypertensives (e.g, clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine). The above list is not meant to be exclusive.

A wide variety of locally active agents can be used in conjunction with the novel excipient described herein, and include both water soluble and water insoluble agents. The locally active agent(s) which may be included in the controlled release formulation of the present invention is intended to exert its effect in the environment of use, e.g., the oral cavity, although in some instances the active agent may also have systemic activity via absorption into the blood via the surrounding mucosa.

The locally active agent(s) include antifungal agents (e.g., amphotericin B, clotrimazole, nystatin, ketoconazole, miconazol, etc.), antibiotic agents (Penicillins, cephalosporins erythromycin, tetracycline, aminoglycosides, etc.), antiviral agents (e.g, acyclovir, idoxuridine, etc.), breath fresheners (e.g. chlorophyll), antitussive agents (e.g., dextromethorphan hydrochloride), anti-cariogenic compounds (e.g., metallic salts of fluoride, sodium monofluorophosphate, stannous fluoride, amine fluorides), analgesic agents (e.g., methylsalicylate, salicylic acid, etc.), local anesthetics (e.g., benzocaine), oral antiseptics (e.g., chlorhexidine and salts thereof, hexylresorcinol, dequalinium chloride, cetylpyridinium chloride), anti-flammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methysalicylate, eucalyptol), acidity reducing agents (e.g., buffering agents such as potassium phosphate lo dibasic, calcium carbonate, sodium bicarbonate, sodium and potassium hydroxide, etc.), and tooth desensitizers (e.g., potassium nitrate). This list is not meant to be exclusive. The solid formulations of the invention may also include other locally active agents, such as flavorants and sweeteners. Generally any flavoring or food additive such as those described in Chemicals Used in Food Processing, pub 1274 by the National Academy of Sciences, pages 63-258 may be used.

A wide variety of pharmaceutically systemically active agents can be formulated e.g., vitamins, minerals, amino acids, essential trace elements, hormones and antagonists thereof, steroids, non-steroid anti-inflammatory agents, antineoplastic agents, antigens, antihistaminic agents, neuropharmacologic agents, including analgesics, vasodilators, anticoagulants, antimicrobial agents, antiviral agents, antifungal agents, antiparasitic agents, heavy metal antagonists, locally active drugs moderating the digestive tract, such as enzymes, antacids, histamine antagonists, diuretics and cardiovascular drugs.

It is to be understood that the compositions of the invention may comprise more than one active drug substance, e.g. a combination of two or more drug substances. For example, a composition of the invention may comprise a therapeutic effective dose of drospirenone and a therapeutic effective dose of an estrogen.

Further constituents of the pharmaceutical compositions according to the invention may include conventional auxiliary substances such as for example antioxidants, binders, emulsifiers, colouring agents, filmforming agents, fillers, odoriferous substances, flavouring substances, gelforming agents, preservatives, solvents, oils, powder bases, ointment bases, acids and salts for the formulation, replenishment and production of pharmaceutical compositions, lubricants, release agents, suppository bases, suspension stabilisers, sweetening agents, effervescent gases, emollients and sugar substitutes.

Plant medicament preparations and homeopathic preparations are also included among the pharmaceutical compositions in which the silicon dioxide Schülpen may be used.

The pharmaceutical compositions according to the invention may also include so-called retard and depot dosage forms with controlled release of active constituent. Moreover the pharmaceutical compositions according to the invention may also be part of therapeutic systems such as for example therapeutic systems for topical application and transdermal therapeutic systems.

In a preferred embodiment the silicon dioxide Schülpen based on pyrogenic silicic acid serves as a glidant for improving the flow of pharmaceutical active constituents and/or excipients and/or mixtures thereof. The present invention is accordingly also directed to a mixture of the aforedescribed silicon dioxide Schülpen and at least one of these substances.

The compositions according to the invention can be used in the form of solid, semi-solid and liquid product forms. Solid product forms are, for example, powders, granules, tablets and filled capsules. Examples of semi-solid product forms are creams, ointments, gels, pastes and "soft" gel capsules. Liquid product forms are, for example, suspensions. Further suitable product forms can be suppositories and aerosols, for example.

The term "glidant" may also mean that silicon dioxide Schülpen or fragments thereof coat solid particles of the material. The forces of attraction between the particles are reduced and for example the flow behaviour is improved.

Schülpen formed from pyrogenic silicic acids can in particular complement or replace the conventional pyrogenic silicic acids that have been established in pharmaceutical practice for many years. For example, Schülpen of pyrogenic silicic acids may above all improve the production and properties of solid medicament forms. Also, they may advantageously be employed in the production of extrudates and replace for example other established auxiliary substances such as cellulose or polymers.

The advantages of the Schülpen based on pyrogenically produced silicon dioxide compared to the known non-granulated pyrogenic silicic acids lie above all in their non-agglomerating behaviour, improved flowability, narrower and definable particle size distribution, and dust-free handling. In addition tablets produced therefrom have mechanical stability and disintegration behaviour properties as do tablets prepared with conventional highly disperse pyrogenic silicic acid.

The invention will now be described in more detail with the aid of examples.

Here too, AEROSIL was first compacted to form Schülpen and then sieve granulated. The fine-material fraction of the subsequent sieving was used. The AEROSIL Schülpen grain size of this fine-material fraction is less than 250 µm.

Highly disperse pyrogenic silicic acids such as AEROSIL 200 Pharma or AEROSIL 200 Pharma VV 120 are frequently used as flow regulators in the production of medicaments. By adding small amounts of AEROSIL, the flow behaviour of an active ingredient carrier or auxiliary substance can be increased and accordingly its application-related properties, such as, for example, its metering ability, can be improved. Avicel PH-101 is a frequently used microcrystalline cellulose whose flow behaviour is improved by addition of small amounts of AEROSIL 200 (e.g. 0.5%). The sieving behaviour and, above all, the sieve residue of the mixture of Avicel and AEROSIL is an important application-related property. A large sieve residue means that automatic weighing, sieving and metering devices cannot be used. In order to test these granules for AEROSIL Schülpen in comparison with AEROSIL 200 Pharma and AEROSIL 200 Pharma VV 120, the sieve residue of the following mixtures was studied.

Avicel® PH-101 without flow regulator (zero sample)
Avicel® PH-101 99.5%+0.5% AEROSIL® 200 Pharma
Avicel® PH-101 99.5%+0.5% AEROSIL® 200 VV Pharma
Avicel® PH-101 99.5%+0.5% AEROSIL Schülpen 250 (x<250 µm)

The various components of the mixture were weighed directly onto a sieve having a mesh size of 0.71 mm. The mixture was first sieved through this sieve and thereby mixed slightly. The pulverulent mixtures were then mixed by means of a mixer (Turbula) at 46 rpm for a defined time (5, 10, 30, 60 minutes). In general, agglomerates break up during mixing, as a result of which the sieving ability generally improves with the mixing time. After the times defined above, the powder was sieved through a 0.315 mm sieve and the sieve residue was determined in wt. %. This is shown in FIG. 8 as a function of the mixing time.

While pure Avicel passes through the sieve completely, the agglomerates in the case of AEROSIL 200 VV 120 Pharma and AEROSIL 200 Pharma are broken up by the mixing process only with difficulty. The sieving ability is relatively poor as a result. AEROSIL 200 VV 120 is compressed on a vacuum press band filter to a tamped density of approximately 120 g/l. However, the sieving behaviour worsens thereby. The AEROSIL Schülpen combine a good sieving and pouring ability with low dust formation. Accordingly, they have marked application-related advantages over AEROSIL 200 Pharma and AEROSIL 200 VV 120 Pharma. Further characteristic values for assessing the flow properties of various auxiliary substances such as microcrystalline cellulose (Avicel PH-101, FMB Biopolymers), starch and lactose monohydrate (Tablettose from Meggle) are AEROSIL Schülpen slightly better or equally as good as in the case of AEROSIL 200 Pharma or AEROSIL 200 VV 120 Pharma.

The AEROSIL Schülpen exhibit a significantly better activity as flow regulators than AEROPERL. The measurement is called angle of repose and is used to determine the flow properties of powders. The angle of repose values are as follows:
Avicel alone: 46.7°
Avicel+1% VP AEROPERL 300 Pharma: 46.70
Avicel+1% AEROSIL® Granulate 500 (250<x<500 µm): 41.0°
Avicel+1% AEROSIL® Granulate 250 (x<250 µm): 37.2°

A difference of 3° in the angle of repose is regarded as significant. AEROPERL produces no improvement in the flowability compared with Avicel alone. The difference of almost 10° between AEROPERL and the AEROSIL Schülpen is an enormous improvement.

The invention claimed is:

1. A pharmaceutical composition comprising a pharmaceutically active ingredient and broken band-like intermediates, said composition is made by the process of de-aerating or decompressing pyrogenically produced silicon dioxide;
  compressing the pyrogenically produced silicon dioxide by roller compaction to form band-like intermediates having a tamped density (according to DIN EN ISO 787-11) of 185 to 700 g/l;
  breaking the band-like intermediates to form the broken band-like intermediates;
  optionally grading or sieving the broken band-like intermediates; and
  combining the broken band-like intermediates with the pharmaceutically active ingredient.

2. The pharmaceutical composition according to claim 1 in the form of a suspension, emulsion, aerosol, ointment, cream, gel, paste, suppository, stick, powder, topical powder, granular material, tablet, pastille, sugar-coated pill, film-coated tablet, hard gelatin capsule, soft gelatin capsule, extrudate, microcapsule or a microsphere.

3. The pharmaceutical composition according to claim 1, wherein the broken band-like intermediates act as a glidant for pharmaceutical active constituents and/or auxiliary substances.

4. The pharmaceutical composition according to claim 1, and further comprising at least one pharmaceutical auxiliary substance.

5. The pharmaceutical composition according to claim 4, wherein the pharmaceutical auxiliary substance is selected from the group consisting of: antioxidants, binders, emulsifiers, colouring agents, film-forming agents, fillers, gel-forming agents, odoriferous substances, flavouring substances, preservatives, solvents, oils, powder bases, ointment bases, acids and salts for the formulation, replenishment and production of pharmaceutical compositions, lubricants, release agents, suppository bases, suspension stabilisers, sweetening agents, effervescent gases, emollients and sugar substitutes.

6. The pharmaceutical composition according to claim 1, wherein the pharmaceutical active ingredient is selected from the group consisting of: a-proteinase inhibitor, abacavir, abciximab, acarbose, acetylsalicylic acid, acyclovir, adenosine, albuterol, aldesleukin, alendronate, alfuzosin, alosetrone, alprazolam, alteplase, ambroxol, amifostine, amiodarone, amisulprid, amlodipine, amoxicillin, amphetamine, amphotericin, ampicillin, amprenavir, anagrelide, anastrozole, ancrod, anti-haemophilia factor, aprotinin, atenolol, atorvastatin, atropine, azelastine, azithromycin, azulene, barnidipin, beclomethasone, benazepril, benserazide, beraprost, betamethasone, betaxolol, bezafibrate, bicalutamide, bisabolol, bisoprolol, botulinum toxin, brimonidine, bromazepam, bromocriptine, budesonide, bupivacaine, bupropion, buspirone, butorphanol, cabergoline, calcipotriene, calcitonin, calcitriol, camphor, candesartan, candesartan cilexetil, captopril, carbamazepine, carbidopa, carboplatin, carvedilol, cefaclor, cefadroxil, cefaxitin, cefazolin, cefdinir, cefepime, cefixime, cefmetazole, cefoperazone, cefotiam, cefoxopran, cefpodoxime, cefprozil, ceftazidime, ceftibuten, ceftriaxone, cefuroxime, celecoxib, celiprolol, cephalexin, cerivastatin, cetirizine, chloramphenicol, cilastatin, cilazapril, cimetidine, ciprofibrate, ciprofloxacin, cisapride, cisplatin, citalopram, clarithromycin, clavulanic acid, clindamycin, clomipramine, clonazepam, clonidine, clopidogrel, clotrimazole, clozapine, cromolyn, cyclophosphamide, cyclosporine, cyproterone, dalteparin, deferoxamine, desogestrel, dextroamphetamine, diazepam, diclofenac, didanosine, digitoxin, digoxin, dihydroergotamine, diltiazem, diphtheria protein, diphtheria toxoide, divalproex, dobutamine, docetaxel, dolasetron, donepezil, dornase-a, dorzolamide, doxazosin, doxifluridin, doxorubicin, dydrogesterone, ecabet, efavirenz, enalapril, enoxaparin, eperisone, epinastin, epirubicin, eptifibatide, erythropoietin-a, erythropoietin-β, etanercept, ethinyl oestradiol, etodolac, etoposide, factor VIII, famciclovir, famotidine, faropeneme, felodipine, fenofibrate, fenoldopam, fentanyl, fexofenadin, filgrastim, finasteride, flomoxef, fluconazole, fludarabine, flunisolide, flunitrazepam, fluoxetine, flutamide, fluticasone, fluvastatin, fluvoxamine, follitropin-a, follitropin-β, formoterol, fosinopril, furosemide, gabapentin, gadodiamide, ganciclovir, gatifloxacin, gemcitabine, gestoden, glatiramer, glibenclamide, glimepiride, glipizide, glyburide, goserelin, granisetron, griseofulvin, hepatitis B antigen, hyaluronic acid, hycosin, hydrochlorothiazide, hydrocodone, hydrocortisone, hydromorphone, hydroxychloroquine, hylan G-F 20, ibuprofen, ifosfamide, imidapril, imiglucerase, imipenem, immunoglobulin, indinavir, indomethacin, infliximab, insulin, insulin human, insulin Lispro, insulin aspart, interferon β, interferon a, iodine 125, iodixanol, iohexyl, iomeprol, iopromid, ioversol, ioxoprolen, ipratropium, ipriflavone, irbesartan, irinotecan, isosorbide, isotretinoin, isradipine, itraconazole, potassium chlorazepate, potassium chloride, ketorolac, ketotifen, whooping cough vaccine, coagulation factor IX, lamivudine, lamotrigine, lansoprazole, latanoprost, leflunomide, lenograstim, letrozole, leuprolide, levodopa, levofloxacin, levonorgestrel, levothyroxine, lidocaine, linezolid, lisinopril, lopamidol, loracarbef, loratadine, lorazepam, losartan, lovastatin, lysineacetylsalicylic acid, manidipin, mecobalamin, medroxyprogesterone, megestrol, meloxicam, menatetrenone, meningococcus vaccine, menotropine, meropenem, mesalamine, metaxalone, metformin, methylphenidate, methylprednisolone, metoprolol, midazolam, milrinone, minocycline, mirtazapine, misoprostol, mitoxantrone, moclobemid, modafinil, mometasone, montelukast, morniflumat, morphine, moxifloxacin, mycophenolate, nabumetone, nadroparin, naproxen, naratriptan, nefazodone, nelfinavir, nevirapine, niacin, nicardipine, nicergoline, nifedipine, nilutamide, nilvadipine, nimodipine, nitroglycerin, nizatidine, norethindrone, norfloxacin, octreotide, olanzapine, omeprazole, ondansetron, orlistate, oseltamivir, oestradiol, oestrogens, oxaliplatin, oxaprozin, oxolinic acid, oxybutynin, paclitaxel, palivizumab, pamidronate, pancrelipase, panipenem, pantoprazol, paracetamol, paroxetine, pentoxifylline, pergolide, phenyloin, pioglitazon, piperacillin, piroxicam, pramipexole, pravastatin, prazosin, probucol, progesterone, propafenone, propofol, propoxyphene, prostaglandin, quetiapine, quinapril, rabeprazol, raloxifene, ramipril, ranitidine, repaglinide, reserpine, ribavirin, riluzole, risperidone, ritonavir, rituximab, rivastigmin, rizatriptan, rofecoxib, ropinirol, rosiglitazone, salmeterol, saquinavir, sargramostim, serrapeptase, sertraline, sevelamer, sibutramin, sildenafil, simvastatin, somatro pine, sotalol, spironolactone, stavudin, sulbactam, sulfaethidole, sulfamethoxazole, sulfasalazin, sulpirid, sumatriptan, tacrolimus, tamoxifen, tamsulosin, tazobactam, teicoplanin, temocapril, temozolomid, tenecteplase, tenoxicam, teprenon, terazosin, terbinafine, terbutaline, tetanus toxoid, tetrabenazine, tetrazepam, thymol, tiagabine, tibolon, ticarcillin, ticlopidine, timolol, tirofiban, tizanidine, tobramycin, tocopheryl nicotinate, tolterodine, topiramate, topotecan, torasemid, tramadol, trandolapril, trastuzumab, triamcinolone, triazolam, trimebutin, trimethoprim, troglitazone, tropisetrone, tulobuterol, unoproston, urofollitropine, valacyclovir, valproic acid, valsartan, vancomycin, venlafaxine, verapamil, verteporfin, vigabatrin, vinorelbine, vinpocetine, vitamin A, vitamin D, vitamin E, vitamin K, voglibose, warfarin, zafirlukast, zaleplon, zanamivir, zidovudine, zolmitriptan, zolpidem, zopiclone, nutritional oils, essential fatty acids, non-essential fatty acids, extracts of plant or animal origin, oils of plant or animal origin and their derivatives.

* * * * *